United States Patent
Licht et al.

[11] Patent Number: 6,063,498
[45] Date of Patent: May 16, 2000

[54] STERILE NONWOVENS BONDED USING POLYURETHANE DISPERSIONS

[75] Inventors: Ulrike Licht, Mannheim; Karl Häberle, Speyer; Peter Claassen; Albrecht Seher, both of Ludwigshafen; Karl-Heinz Schumacher, Neustadt; Hermann Seyffer, Heidelberg, all of Germany

[73] Assignee: BASF Aktiengesellschaft, Ludwigshafen, Germany

[21] Appl. No.: 09/184,905

[22] Filed: Nov. 3, 1998

[30] Foreign Application Priority Data

Dec. 8, 1997 [DE] Germany .................. 197 54 300

[51] Int. Cl.⁷ .................. B05D 3/00; B32B 1/04; B32B 3/02; B32B 27/00; D06N 7/04
[52] U.S. Cl. .................. 428/423.1; 427/2.31; 428/76; 428/142; 428/195; 602/45; 602/52
[58] Field of Search .................. 428/423.1, 76, 428/142, 195; 602/45, 52; 427/2.31

[56] References Cited

U.S. PATENT DOCUMENTS

| | | | |
|---|---|---|---|
| 4,204,532 | 5/1980 | Lind et al. | 128/132 D |
| 4,705,712 | 11/1987 | Cashaw et al. | 428/152 |

FOREIGN PATENT DOCUMENTS

| | | |
|---|---|---|
| 0 147 759 A2 | 7/1985 | European Pat. Off. . |
| 0 319 386 A2 | 6/1989 | European Pat. Off. . |
| 0 505 775 A2 | 9/1992 | European Pat. Off. . |

*Primary Examiner*—Patrick D. Niland
*Attorney, Agent, or Firm*—Oblon, Spivak, McClelland, Maier & Neustadt, P.C.

[57] ABSTRACT

A process for producing sterile nonwovens comprises a textile fabric composed of a fiber web being impregnated with an aqueous dispersion comprising a polyurethane, then dried and irradiated with γ-rays.

5 Claims, No Drawings

STERILE NONWOVENS BONDED USING POLYURETHANE DISPERSIONS

The present invention relates to a process for producing sterile nonwovens, which comprises a textile fabric composed of a fiber web being impregnated with an aqueous dispersion comprising a polyurethane, then dried and irradiated with γ-rays, to the nonwovens themselves and also to sterile medical articles composed of these nonwovens.

Nonwovens obtained when a textile sheet material (web) is impregnated with an aqueous dispersion comprising a polymer and then dried are common knowledge (cf. Ullmann's Encyclopädie der technischen Chemie, 4th edition, Verlag Chemie, Weinheim 1983, Volume 23, Vliesstoffe, pages 729ff). More particularly, page 733 of the cited reference recommends using polyurethane dispersions as nonwoven binders.

Existing nonwoven binder dispersions make it possible to produce nonwovens having the properties which are important for most applications such as breaking strength, softness, resistance to fluids, especially body fluids, and the right balance of hydrophilicity and hydrophobicity for the particular application. Some of the dispersions have also been optimized to allow the nonwovens bonded therewith to be sterilized with γ-rays without significantly impairing the aforementioned properties.

Sterilization with γ-rays is of particular importance in the case of articles for use in the medical sector or as hygiene articles. Examples are clean supply room articles such as medical head covers, OR mouthguards, OR gowns, overshoes, OR table drapes, OR patient drapes, OR cloths, OR swabs, wrapping cloths for surgical instruments, etc., but also packaging nonwovens for food and the like. In the case of medical applications, the nonwovens are customarily packed in PE bags, sealed and sterilized with γ-rays. When needed, the bags are pulled open and the articles removed.

EP-A-0 319 386 describes nonwovens comprising a free radical scavenger as stabilizer. It is a long chain aliphatic ester of 3,5-di-t-butyl-4-hydroxybenzoic acid, which upon irradiation with ionizing rays first inhibits odoriferousness and secondly lessens the strength loss of the nonwoven.

EP-A-0 505 775 describes the use of a light stabilizer (UV-absorber) in polypropylene nonwoven composites to improve γ-ray stability. The light stabilizer in question is an acetylated, sterically hindered amine which may be substituted by a siloxane oligomer (polymethylpropyl-3-oxy[4-(2, 2,6,6-tetra-methyl)piperidinyl]siloxane).

EP-A-0 147 759 describes a sterilizable nonwoven consolidated using an acrylate-based (-containing) binder which acquires utility as a nonwoven binder through methylol crosslinking. The improved sterilization stability is obtained via antioxidants of the amine type and hindered phenols.

The aforementioned nonwovens have the disadvantage that, notwithstanding the use of light stabilizers or free radical scavengers, they still tend to release strongly malodorous substances upon sterilization by irradiation. This is particularly unpleasant and particularly strongly noticeable when airtight packages of the sterilized articles are opened.

It is an object of the present invention to provide processes for producing nonwovens and for producing nonwoven articles which can be used in the medical sector or as hygiene articles and also these nonwoven articles themselves. These articles shall be sterilizable using γ-rays especially without the creation of foul odors.

We have found that this object is achieved by the matters defined at the beginning.

The aqueous dispersions useful for producing the nonwovens of the present invention are in particular aqueous dispersions of self dispersing polyurethanes. Such polyurethanes are capable of forming a fine dispersion in water without the presence of effective amounts of additional dispersing aids such as emulsifiers. Such dispersions are generally polymerized from a) diisocyanates having from 4 to 30 carbon atoms, b) diols, of which b1) from 10 to 100 mol %, based on total diols (b), have a molecular weight within the range from 500 to 5000, and b2) from 0 to 90 mol %, based on total diols (b), have a molecular weight within the range from 60 to 500 g/mol, c) monomers that differ from said monomers (a) and (b) and have one or more isocyanate or isocyanate reactive groups and additionally bear one or more hydrophilic or potentially hydrophilic groups to render the polyurethanes water dispersible, d) optionally further polyfunctional compounds which differ from said monomers (a) to (c) and have reactive groups comprising alcoholic hydroxyl groups, primary or secondary amino groups or isocyanate groups, and e) optionally monofunctional compounds which differ from said monomers (a) to (d) and have a reactive group comprising an alcoholic hydroxyl group, a primary or secondary amino group or an isocyanate group.

As monomers (a) it is possible to use the diisocyanates customarily used in polyurethane chemistry.

Particular diisocyanates are diisocyanates $X(NCO)_2$, where X is aliphatic hydrocarbyl having from 4 to 12 carbon atoms, a cycloaliphatic or aromatic hydrocarbyl having from 6 to 15 carbon atoms or araliphatic hydrocarbyl having from 7 to 15 carbon atoms. Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis-(4-isocyanatocyclohexyl)propane, trimethylhexane diisocyanate, 1,4-diisocyanatobenzene, 2,4-diisocyanatotoluene, 2,6-diisocyanatotoluene, 4,4'-diisocyanatodiphenylmethane, 2,4'-diisocyanatodiphenylmethane, p-xylylene diisocyanate, tetramethylxylylene diisocyanate (TMXDI), the isomers of bis(4-isocyanatocyclohexyl)methane (HMDI) such as the trans/trans, the cis/cis and the cis/trans isomers, and also mixtures thereof.

Suitable mixtures of these isocyanates are particularly the mixtures of the respective structural isomers of diisocyanatotoluene and diisocyanatodiphenylmethane, especially the mixture of 80 mol % of 2,4 diisocyanatotoluene and 20 mol% of 2,6-diisocyanatotoluene. Furthermore, the mixtures of aromatic isocyanates such as 2,4-diisocyanatotoluene and/or 2,6-diisocyanatotoluene with aliphatic or cycloaliphatic isocyanates such as hexamethylene diisocyanate or IPDI are particularly advantageous, the preferred mixing ratio of aliphatic to aromatic isocyanates being within the range from 4:1 to 1:4.

As compounds (a) it is also possible to use isocyanates which, as well as free isocyanate groups, bear capped isocyanate groups, e.g., uretdione or carbodiimide groups.

With regard to good filming and elasticity, suitable diols (b) are primarily higher molecular weight diols (b1) having a molecular weight of from about 500 to 5000, preferably of from about 1000 to 3000, g/mol.

The diols (b1) are especially polyesterpolyols, which are known for example from Ullmann's Encyklopädie der technischen Chemie, 4th edition, Volume 19, pages 62 to 65. Preference is given to using polyesterpolyols which are obtained by reaction of dihydric alcohols with dibasic carboxylic acids. Instead of the free polycarboxylic acids it is also possible to use the corresponding polycarboxylic anhydrides or corresponding polycarboxylic esters of lower alcohols or mixtures thereof for preparing the polyesterpolyols. The polycarboxylic acids can be aliphatic, cycloaliphatic, araliphatic, aromatic or heterocyclic and can be unsaturated and/or substituted, for example by halogen atoms. Examples are suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric fatty acids. Preference is given to dicarboxylic acids of the general formula $HOOC-(CH_2)_y-COOH$, where y is from 1 to 20, preferably an even number from 2 to 20, e.g., succinic acid, adipic acid, dodecanedicarboxylic acid and sebacic acid.

Suitable polyhydric alcohols include, for example, ethylene glycol, 1,2-propanediol, 1,3-propanediol, 1,3-butanediol, 1,4-butenediol, 1,4-butynediol, 1,5-pentanediol, neopentylglycol, bis(hydroxymethyl)cyclohexanes such as 1,4-bis(hydroxymethyl) cyclohexane, 2-methylpropane-1,3-diol, methylpentanediols, also diethylene glycol, triethylene glycol, tetraethylene glycol, polyethylene glycol, dipropylene glycol, polypropylene glycol, dibutylene glycol and polybutylene glycols. Preference is given to alcohols of the general formula $HO-(CH_2)_x-OH$, where x is from 1 to 20, preferably an even number from 2 to 20. Examples thereof are ethylene glycol, 1,4-butanediol, 1,6-hexanediol, 1,8-octanediol and 1,12-dodecanediol.

Also suitable are polycarbonatediols as are obtainable, for example, by reaction of phosgene with an excess of the low molecular weight alcohols mentioned as formative components for the polyesterpolyols.

It is also possible to use lactone-based polyesterdiols, i.e., homo- or copolymers of lactones, preferably terminally hydroxyl-functional addition products of lactones on suitable difunctional initiator molecules. Preferred lactones are derived from compounds of the general formula $HO-(CH_2)_z-COOH$, where z is from 1 to 20 and an H atom of a methylene unit may also be replaced by a $C_1-C_4$-alkyl radical. Examples are $\epsilon$-caprolactone, $\beta$-propiolactone, $\gamma$-butyrolactone and/or methyl-$\epsilon$-caprolactone and also mixtures thereof. Suitable initiator components include, for example, the low molecular weight dihydric alcohols mentioned above as formative components for the polyesterpolyols. The corresponding addition polymers of $\epsilon$-caprolactone are particularly preferred. Similarly, lower polyesterdiols or polyetherdiols can be used as initiators for preparing the lactone addition polymers. Instead of the addition polymers of lactones it is also possible to use the corresponding, chemically equivalent polycondensates of the hydroxycarboxylic acids corresponding to the lactones.

Useful monomers (b1) further include polyetherdiols. They are obtainable in particular by homopolymerization of ethylene oxide, propylene oxide, butylene oxide, tetrahydrofuran, styrene oxide or epichlorohydrin, for example in the presence of $BF_3$, or by the addition of these compounds, optionally mixed or in succession, to initiating components having reactive hydrogen atoms, such as alcohols or amines, e.g., water, ethylene glycol, 1,2-propanediol, 1,3-propanediol, 1,2-bis(4-hydroxydiphenyl) propane or aniline. Particular preference is given to polytetrahydrofuran having a molecular weight of from 240 to 5000, especially from 500 to 4500.

Also suitable are polyhydroxyolefins, preferably those having 2 terminal hydroxyl groups, for example $\alpha,\omega$-dihydroxypolybutadiene, $\alpha,\omega$-dihydroxypolymethacrylic esters or $\alpha,\omega$-dihydroxy polyacrylic esters, as monomer (c1). Such compounds are known from EP-A-0622378, for example. Further suitable polyols are polyacetals, polysiloxanes and alkyd resins.

The polyols can also be used as mixtures in a ratio of from 0.1:1 to 1:9.

The hardness and the modulus of elasticity of the polyurethanes can be increased by using as diols (b) not only diols (b1) but additionally low molecular weight diols (b2) having a molecular weight of from about 62 to 500, preferably from 62 to 200, g/mol.

Useful monomers (b2) include especially the formative components for the short chain alkanediols mentioned for preparing polyesterpolyols, preference being given to the unbranched diols having from 2 to 12 carbon atoms and an even number of carbon atoms and also to 1,5-pentanediol.

The proportion of diols (b1), based on total diols (b), is from 10 to 100 mol % and the proportion of monomers (b2), based on total diols (b), is from 0 to 90 mol %. The ratio of diols (b1) to monomers (b2) is particularly preferably within the range from 0.1:1 to 5:1, particularly preferably within the range from 0.2:1 to 2:1.

To render the polyurethanes water dispersible, they are polymerized not only from the components (a), (b) and (d) but also from monomers (c) which differ from components (a), (b) and (d) and which bear one or more isocyanate or isocyanate reactive groups and additionally at least one hydrophilic group or a group which is convertible into a hydrophilic group. In what follows, the expression "hydrophilic groups or potentially hydrophilic groups" is abbreviated to "(potentially) hydrophilic groups". The (potentially) hydrophilic groups react significantly more slowly with isocyanates than the functional groups of the monomers which serve to polymerize the polymer backbone.

The proportion of the total amount of components (a), (b), (c), (d) and (e) which is attributable to components having (potentially) hydrophilic groups is generally determined so that the molar amount of the (potentially) hydrophilic groups is from 30 to 1000, preferably from 50 to 500, particularly preferably from 80 to 300, mmol/kg, based on the weight of all monomers (a) to (e).

The (potentially) hydrophilic groups are nonionic or preferably (potentially) ionic hydrophilic groups.

Suitable nonionic hydrophilic groups include in particular polyethylene glycol ethers containing preferably from 5 to 100, preferably from 10 to 80, ethylene oxide repeat units. The level of polyethylene oxide units is generally within the range from 0 to 10, preferably from 0 to 6, % by weight, based on the weight of all monomers (a) to (e).

Preferred monomers with nonionic hydrophilic groups are polyethylene oxide diols, polyethylene oxide monools and also the reaction products of a polyethylene glycol and a diisocyanate which bear a terminally etherified polyethylene glycol radical. Such diisocyanates and methods for their preparation are described in U.S. Pat. No. 3,905,929 and U.S. Pat. No. 3,920,598.

Ionic hydrophilic groups include in particular anionic groups such as the sulfonate, the carboxylate and the phosphate group in the form of their alkali metal or ammonium salts and also cationic groups such as ammonium groups, especially protonated tertiary amino groups or quaternary ammonium groups.

Potentially ionic hydrophilic groups are in particular those which can be converted by simple neutralization, hydrolysis or quaternization reactions into the abovementioned ionic hydrophilic groups, e.g., carboxylic acid groups, anhydride groups or tertiary amino groups.

(Potentially) ionic monomers (c) are extensively described for example in Ullmann's Encyklopädie der technischen Chemie, 4th edition, Volume 19, pages 311–313, and, for example, in DE-A 1 495 745.

(Potentially) cationic monomers (c) of particular practical importance are in particular monomers having tertiary amino groups, for example tris(hydroxyalkyl)amines, N,N'-bis(hydroxyalkyl)alkylamines, N-hydroxyalkyldialkylamines, tris-(aminoalkyl)amines, N,N'-bis(aminoalkyl)alkylamines, N-aminoalkyldialkylamines, the alkyl radicals and alkanediyl units of these tertiary amines containing from 1 to 6 carbon atoms independently of each other. Also suitable are polyethers having tertiary nitrogen atoms and preferably two terminal hydroxyl groups, as are obtainable in a conventional manner, for example, by alkoxylation of amines having two hydrogen atoms attached to amine nitrogen, e.g., methylamine, aniline or N,N'-dimethylhydrazine. Such polyethers generally have a molecular weight within the range from 500 to 6000 g/mol.

These tertiary amines are converted into the ammonium salts either with acids, preferably strong mineral acids such as phosphoric acid, sulfuric acid, halohydric acids, or strong organic acids, or by reaction with suitable quaternizing agents such as $C_1$–$C_6$-alkyl halides or benzyl halides, for example bromides or chlorides.

Suitable monomers with (potentially) anionic groups customarily include aliphatic, cycloaliphatic, araliphatic or aromatic carboxylic acids and sulfonic acids which bear at least one alcoholic hydroxyl group or at least one primary or secondary amino group. Preference is given to dihydroxyalkylcarboxylic acids, especially having from 3 to 10 carbon atoms, as also described in U.S. Pat. No. 3,412,054. Particular preference is given to compounds of the general formula

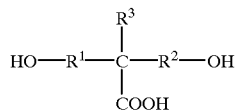

where $R^1$ and $R^2$ are each a $C_1$–$C_4$-alkanediyl unit and $R^3$ is a $C_1$–$C_4$-alkyl unit, and especially dimethylolpropionic acid (DMPA).

Also suitable are the corresponding dihydroxysulfonic acids and dihydroxyphosphonic acids such as 2,3-dihydroxypropanephosphonic acid.

It is also possible to use dihydroxy compounds having a molecular weight of from above 500 to 10,000 g/mol and at least 2 carboxylate groups, known from DE-A 3 911 827. They are obtainable by reaction of dihydroxy compounds with tetracarboxylic dianhydrides such as pyromellitic dianhydride or cyclopentanetetracarboxylic dianhydride in a molar ratio of from 2:1 to 1.05:1 in a polyaddition reaction. Suitable dihydroxy compounds are in particular the monomers (b2) cited as chain extenders and also the diols (b1).

Suitable monomers (c) with isocyanate reactive amino groups are amino acids such as lysine, β-alanine, the adducts, mentioned in DE-A-2034479, of aliphatic diprimary diamines with α,β-unsaturated carboxylic or sulfonic acids.

Suitable monomers (c) with isocyanate reactive amino groups are amino acids such as lysine, β-alanine, the adducts, mentioned in DE-A-2034479, of aliphatic diprimary diamines with α,β-unsaturated carboxylic or sulfonic acids.

Such compounds conform for example to the formula (d1)

$$H_2N-R^4-NH-R^5-X \qquad (d1)$$

where $R^4$ and $R^5$ are independently a $C_1$–$C_6$-alkanediyl unit, preferably ethylene, and X is COOH or $SO_3H$.

Particularly preferred compounds of the formula (d1) are N-(2-aminoethyl)-2-aminoethanecarboxylic acid and N-(2-aminoethyl)-2-aminoethanesulfonic acid and the corresponding alkali metal salts, sodium being particularly preferred as counterion. Particular preference is also given to the adducts of the abovementioned aliphatic diprimary diamines with 2-acrylamido-2-methylpropanesulfonic acid, as described in D 1 954 090, for example.

If monomers having potentially ionic groups are used, their conversion into the ionic form can take place before, during, but preferably after the isocyanate polyaddition reaction, since ionic monomers are frequently only sparingly soluble in the reaction mixture. The carboxylate or sulfonate groups are particularly preferably present in the form of their salts with an alkali metal ion or an ammonium ion as counterion.

The monomers (d), which differ from the monomers (a) to (c), generally serve the purpose of crosslinking or of chain extension. They are generally more than dihydric nonphenolic alcohols, amines having 2 or more primary and/or secondary amino groups and also compounds which bear one or more primary and/or secondary amino groups alongside one or more alcoholic hydroxyl groups.

Alcohols having a hydricness higher than 2, which can be used to set a certain degree of branching or crosslinking, are, for example, trimethylolpropane, glycerol or sugars.

It is also possible to use monoalcohols which, as well as the hydroxyl group, bear a further isocyanate reactive group such as monoalcohols having one or more primary and/or secondary amino groups, e.g., monoethanolamine.

Polyamines having 2 or more primary and/or secondary amino groups are used in particular when the chain extension or crosslinking is to take place in the presence of water, since amines generally react faster with isocyanates than alcohols or water. This is frequently necessary when aqueous dispersions of crosslinking polyurethanes or polyurethanes having a high molecular weight are desired. In such cases, prepolymers with isocyanate groups are prepared, rapidly dispersed in water and subsequently chain extended or crosslinked by addition of compounds having a plurality of isocyanate reactive amino groups.

Suitable amines for this purpose are generally polyfunctional amines of the molecular weight range from 32 to 500 g/mol, preferably from 60 to 300 g/mol, which contain at least two amino groups selected from the group of the primary and secondary amino groups. Examples thereof are diamines such as diaminoethane, diaminopropanes, diaminobutanes, diaminohexanes, piperazine, 2,5-dimethylpiperazine, amino-3-aminomethyl-3,5,5-trimethyl cyclohexane (isophoronediamine, IPDA), 4,4'-diaminodicyclo hexylmethane, 1,4-diaminocyclohexane, aminoethylethanolamine, hydrazine, hydrazine hydrate or triamines such as diethylenetriamine or 1,8-diamino-4-aminomethyloctane.

The amines can also be used in blocked form, for example in the form of the corresponding ketimines (see for example CA-1 129 128), ketazines (cf. for example U.S. Pat. No. 4,269,748) or amine salts (see U.S. Pat. No. 4,292,226). Similarly, oxazolidines as used in U.S. Pat. No. 4,192,937, for example, are capped polyamines which can be used to chain extend the prepolymers in the preparation of the polyurethanes of the present invention. When such capped polyamines are used, they are generally mixed with the prepolymers in the absence of water and this mixture is subsequently mixed with the dispersion water or a portion of the dispersion water, so that the corresponding polyamines are released hydrolytically.

Preference is given to using mixtures of di- and triamines, particularly preferably mixtures of isophoronediamine and diethylenetriamine.

The polyurethanes preferably contain no polyamine or from 1 to 10, particularly preferably from 4 to 8, mol %, based on the total amount of components (b) and (d), of a polyamine having at least 2 isocyanate reactive amino groups as monomer (d).

Alcohols having a hydricness higher than 2, which can be used to set a certain degree of branching or crosslinking, are, for example, trimethylolpropane, glycerol or sugars.

Trifunctional and tetrafunctional isocyanates can be used for the same purpose as monomers (d). Examples of commercially available compounds are the isocyanurate or the biuret of hexamethylene diisocyanate.

Monomers (e), the use of which is optional, are monoisocyanates, monoalcohols and monoprimary and secondary amines. In general, their proportion will be not more than 10 mol %, based on the total monomers. These monofunctional compounds customarily bear further functional groups such as olefinic groups or carbonyl groups and serve to introduce into the polyurethane the functional groups which make possible the dispersing or the crosslinking or further polymer-analogous reaction of the polyurethane. Suitable for this purpose are monomers such as isopropenyl a,a-dimethylbenzyl isocyanate (TMI) and esters of acrylic or methacrylic acid such as hydroxyethyl acrylate or hydroxyethyl methacrylate.

In the field of polyurethane chemistry it is common knowledge how the molecular weight of the polyurethanes can be set via the choice of the proportions of the mutually reactive monomers and via the arithmetic mean of the number of reactive functional groups per molecule.

The components (a) to (e) and also their respective molar quantities are normally chosen so that the ratio A:B where A) if the molar quantity of isocyanate groups and
B) if the sum total of the molar quantity of hydroxyl groups and the molar quantity of functional groups capable of reacting with isocyanates in an addition reaction is within the range from 0.5:1 to 2:1, preferably within the range from 0.8:1 to 1.5, particularly preferably within the range from 0.9:1 to 1.2:1. The ratio of A:B is most preferably very close to 1:1.

The monomers (a) to (e) used bear on average typically from 1.5 to 2.5, preferably from 1.9 to 2.1, particularly preferably 2.0, isocyanate groups or functional groups capable of reacting with isocyanates in an addition reaction.

The polyaddition of components (a) to (e) is generally effected at reaction temperatures from 20 to 180° C., preferably from 50 to 150° C., under atmospheric pressure or under autogenous pressure.

The requisite reaction times can range from a few minutes to several hours. In the field of polyurethane chemistry it is known how the reaction time is affected by a multiplicity of parameters such as temperature, concentration of the monomers, reactivity of the monomers.

The reaction of the diisocyanates can be catalyzed using customary catalysts, such as dibutyltin dilaurate, tin(II) octoate or diazabicyclo[2.2.2]octane.

A suitable apparatus for carrying out the polymerization is a stirred tank, especially when solvents are used to ensure a low viscosity and good heat removal.

If the reaction is carried out with a solvent, the usually high viscosities and the usually only short reaction times mean that typically extruders are suitable, especially self-cleaning multiscrew extruders.

Preferred solvents are miscible with water in any proportion, have an atmospheric pressure boiling point within the range from 40 to 100° C. and react only slowly, if at all, with the monomers.

The dispersions are usually prepared by one of the following processes:

In the acetone process, an ionic polyurethane is prepared from components (a) to (c) in a water-miscible solvent having an atmospheric pressure boiling point of below 100° C. Sufficient water is added to form a dispersion in which water is the coherent phase.

The prepolymer blending process differs from the acetone process in that the initial product is not a fully reacted (potentially) ionic polyurethane but a prepolymer which bears isocyanate groups. The components here are chosen so that the defined A:B ratio is within the range from greater than 1.0 to 3, preferably within the range from 1.05 to 1.5. The prepolymer is first dispersed in water and then, if desired, crosslinked by reaction of the isocyanate groups with amines bearing more than 2 isocyanate reactive amino groups or chain extended with amines bearing 2 isocyanate reactive amino groups. Chain extension takes place even when no amine is added. In this case, isocyanate groups are hydrolyzed to amino groups which react with any remaining isocyanate groups of the prepolymers to effect chain extension.

If a solvent was used in the synthesis of the polyurethane, most of it is typically removed from the dispersion, for example by distillation under reduced pressure. The dispersions preferably have a solvent content of less than 10% by weight and are particularly preferably free from solvent.

The dispersions generally have a solids content from 10 to 75, preferably from 20 to 65, % by weight and a viscosity of from 10 to 500 mPas (measured at 20° C. and a shear rate of 250 s$^{-1}$).

Hydrophobic auxiliaries which may be difficult to disperse homogeneously in the finished dispersion, for example phenol condensation resins of aldehydes and phenol or phenol derivatives or epoxy resins and further polymers, mentioned for example in DE-A-3903538, 43 09 079 and 40 24 567, serving as adhesion improvers, for example, in polyurethane dispersions, can be added to the polyurethane or the prepolymer before the dispersing step, according to the methods described in the two abovementioned references.

It is usually not necessary to add effective amounts of light stabilizers to avoid the appearance of odors or any deterioration in the mechanical properties.

The polyurethane dispersions may comprise commercially available assistants and additives such as blowing agents, defoamers, emulsifiers, thickeners, thixotropicizers and colorants such as dyes and pigments.

Suitable textile fabrics composed of fiber web (hereinafter abbreviated to "web") for producing the nonwovens of the present invention include all which come within the definition given in German standard specification DIN 61210 of January 1982. Such webs are also described, for example, in section 2.1 on pages 729ff of then nonwovens chapter in volume 23 of Ullmann's Encyclopädie der technischen Chemie, 4th edition, Verlag Chemie, Weinheim 1983.

The webs preferably comprise materials such as viscose, polyester, pulp, cellulose, polypropylene or polyamide. Staple fibers, short cut fibers and continuous filament fibers are all suitable.

The web can be impregnated by the commonly known methods, for example by the webs being dipped into, pulled through or sprayed with the polyurethane dispersion and excess dispersion then being sucked off or squeezed off (cf. pages 738 and 739 loc. cit.). The amount of polyurethane dispersion with which the web is impregnated is chosen so that the fibrous, porous structure of the web is essentially preserved and the fibers are mainly only mutually adhered at the cross-over points. This generally requires from 15 to 40, preferably from 25 to 35, g of polyurethane dispersion solid per 100 g of web. These coatings must be distinguished from coatings where an unbroken film is produced on the web or the web has been completely embedded in the coating material, producing a continuous, more or less pore-free structure without fibrous hand.

After drying, the nonwovens are generally converted into hygiene articles or into articles used in the medical sector (medical articles).

The type of medical article contemplated here is known, for example, from the following articles: "A study of the Effect of Sterilizing Radiation on Nonwovens Using Electron Beam and Gamma Sources", Int. Nonwovens J., Vol. 7, No. 2, pages 71 to 81; "Hospital/Medical Applications for Polyolefin Nonwoven Products", Nonwovens Industry, November, 1989, pages 40 to 43; "Better Medicine through Nonwovens", Nonwovens Industry, October, 1991, page 21; "Medical Nonwovens. A Wait and See View from the Industry", Nonwovens Industry, October, 1991, page 24; "Medical Textiles: The Role of Nonwovens", Nonwovens Industry, October, 1991, page 22.

Examples of articles of this type are clean supply room articles such as medical headguards, OR mouthguard, OR gowns, overshoes, OR table drapes, OR patient drapes, OR cloths, OR swabs, wrapping cloths for surgical instruments, etc., but also packaging webs for foods and the like.

After the nonwoven articles have been produced, they are generally packaged in customary packaging materials such as plastic films or metal foils which are impervious to the penetration of microorganisms in order that any poststerilization recontamination of the articles with germs may be ruled out.

Particularly suitable packaging materials are aluminum foils, polyethylene films and polypropylene films.

Packaging is effected in a conventional manner, for example by packing the nonwoven articles into film bags and thermally sealing these bags by partially melting the plastic material.

It is similarly possible firstly to sterilize the nonwoven materials and then to package them in a sterile room by the abovementioned method.

Sterilization with γ-rays is likewise common knowledge. A suitable source of γradiation is $^{60}$Co in particular.

In general, energy doses from 20 to 40 kGy are required. The dose rate is typically within the range from 2 to 6 kGy/h. Suitable radiation machines of industrial operators of $^{60}$Co machines of about 100 PBq (2.5 Mci) provide a dose rate of 4 kGy/h.

Experimental Part
A. Preparation of Polyurethane Dispersions

EXAMPLE 1

200 g (0.10 mol) of an OH number 56 polyesterol formed from adipic acid, hexanediol and neopentylglycol, 200 g of acetone and 40.5 g (0.45 mol) of 1,4-butanediol were charged into a stirred tank. At 80° C. a mixture of 69.70 g (0.40 mol) of toluylene diisocyanate and 33.6 g (0.20 mol) of hexamethylene diisocyanate and also 0.02 g of dibutyltin dilaurate was added, and the batch was stirred at 60° C. for 180 min. It was then diluted with 300 g of acetone and at the same time cooled to 50° C. The NCO content of the solution was found to be 0.51%. 19.3 g (0.05 mol) of a 40% strength aqueous solution of the sodium salt of 2-(2-aminoethyl) aminoethanecarboxylic acid were then added. 500 g of water were added after 15 minutes. Distillation of the acetone afforded a fine PUR dispersion having a solids content of 41%.

Comparative Dispersion

The customary method of free radical emulsion polymerization (see Vollmert, Grundriss der Makromolekulare Chemie, E. Vollmert Verlag, Karlsruhe 1988) was employed. The emulsifier used was a sulfated fatty alcohol ethoxylate based on a $C_{12}$ fatty acid and containing an average of 30 ethylene oxide units. 0.5% of emulsifier was used, based on the polymer mass. 0.2% of sodium persulfate was used as initiator. The monomers used are reported under B.

B. Preparation of Dispersion Bonded Nonwovens

The web material used was a commercially available pulp/polyester web of about 45–55 g/m$^2$. The ratio of pulp to polyester is about 80:20. Such web styles are customarily used for medical nonwovens.

Strips of the unbonded web 35–50 cm in length and 25–28 cm in width were pulled through an impregnating bath and passed over an aspirating means. This was followed by drying at 150° C. for 2 minutes. The solids content of the dispersion was adjusted in such a way (impregnating liquor) that the binder add-on after drying was about 30% (fiber to binder 3.3:1). (Details see C, test methods)

The nonwovens were produced using the following binders:

1) formaldehyde-free binder based on polyurethane of Example 1
2) formaldehyde-free model binder, composition 100 EA
3) formaldehyde-free model binder, composition 90 BA/10 AN
4) commercially available binder based on BA/AN (Acronal® DS 2285 X from BASF AG)
5) binder-free unbonded web The results of the application tests carried out according to the test methods specified under C are reported under D C. Test Methods
Breaking Strengths Dry and Wet Test strips 140×50 mm in both length and width are ruptured in a tensile tester partly in the dry state, partly after 60 min water aging with 0.1% wetting agent. The respective results are averages of 5 individual tests (see test methods)

Stiffness Test

Bending stiffness is determined using a special instrument. Bending stiffness is the force required to bend a web specimen (30×70 mm) over a mandrel.

Radiation Procedure

A 3.0 g web sample is placed into a ½ L ground joint glass flask and irradiated with a $^{60}$Co source. The parameters are: dose rate 45 mGy/s; irradiation time 183 h. This amounts to a dose of 30 kGy. The glass flasks are located around the source at a radius of 17 cm; they are irradiated at room temperature.

Odor Test Procedure

The sealed glass flasks are stored in a conditioning room (23° C./50% relative humidity) for one day. The test panel is made up of about 10 people. Each tester sniffs individually from the flasks, reseals them at once and rates the odor sensation on a scale from 1 to 5 with no intermediate values. The next tester may not be admitted until 30 min has elapsed. Each odor test includes a number of standard comparisons, for example unbonded web and a conventional binder. The ratings are:

1: no detectable odor
2: slight detectable odor
3: medium odor
4: strong odor
5: extreme odor D. Testing of Application Properties of Nonwovens

TABLE 1

Evaluation of odor

| Specimen | Odor prior to irradiation | Odor after irradiation |
| --- | --- | --- |
| 2. 100 EA (model) | 1.7 | 2.9 |
| 3. 90 BA / 10 AN (model) | 2 | 3.6 |
| 1. Polyurethane Example 1 | 1.7 | 2.0 |
| 4. Commercial binder | 2.2 | 3.8 |
| 5. Unbonded web (pulp/polyester) Polyester) | 1.5 | 2.0 |

TABLE 2

Evaluation of binder properties prior to sterilization

| Specimen | Dry breaking strength | Wet breaking strength | Stiffness |
| --- | --- | --- | --- |
| 1. Polyurethane Example 1 | 143 [N/50 mm] | 84 [N/50 mm] | 200 mN |
| 4. Commercial binder | 124 [N/50 mm] | 55 [N/50 mm] | 166 mN |

TABLE 3

Binder properties after sterilization in % of original value

| Specimen | Dry breaking strength | Wet breaking strength |
| --- | --- | --- |
| 1. Polyurethane Example 1 | 87.5% | 81% |
| 4. Commercial binder | 44.4% | 92% |

Result

Table 1 shows that a commercial binder based on BA/AN (Acronal DS 2285 X) and a similarly constructed model binder develop considerable odor on radiation sterilization, the rating deteriorating by 1.5 points. The comparative specimen with 100% EA develops a similar amount of odor on irradation: in this case, the rating deteriorates by about one point. The web specimen impregnated with the polyurethane behaves in the same way as the unbonded web, whose odor deteriorates by about half a rating point as a result of irradiation. This compels the conclusion that, in this case, the odor is exclusively due to the fiber and not due to the binder. The polyurethane binder thus did not develop any odor on irradiation.

Table 2 reveals that the binder properties of the polyurethane binder are equivalent to those of a commercial product which is used as a web binder (Acronal DS 2285 X). The model dispersions are not useful as binders; they have therefore been omitted from the table.

Table 3 reveals that the polyurethane binder performs better than the acrylate binder with regard to strength retention after irradiation, too: After a radiation dose of 30 kGy, the dry breaking strength is 87.5% of the original level. True, the wet breaking strength decreased somewhat more than in the case of the acrylate binder, but in this case the original level of the latter was distinctly lower, so that the PUR binder is superior in this respect, too.

E. Abbreviations

EA=Ethyl acrylate
AN=Acrylonitrile
BA=Butyl acrylate
PUR=Polyurethane

We claim:

1. A process for producing sterile nonwovens, which comprises a textile fabric composed of a fiber web being impregnated with an aqueous dispersion comprising a polyurethane, then dried and irradiated with γ-rays, wherein the polyurethane used is polymerized from a) diisocyanates having from 4 to 30 carbon atoms,
b) diols, of which
   b1) from 10 to 100 mol %, based on total diols (b), have a molecular weight within the range from 500 to 5000, and
   b2) from 0 to 90 mol %, based on total diols (b), have a molecular weight within the range from 60 to 500 g/mol,
c) monomers of the formula (d1)

$$H_2N—R^4—NH—R^5—X \qquad (d1)$$

where
R$^4$ and R$^5$ are independently a $C_1$–$C_6$-alkanediyl unit, and X is COOH or a carboxylate group in the form of their salts with an alkali metal ion or an ammonium ion as counterion, d) optionally further polyfunctional compounds which differ from said monomers (a) to (c) and have reactive groups comprising alcoholic hydroxyl groups, primary or secondary amino groups or isocyanate groups, and e) optionally monofunctional compounds which differ from said monomers (a) to (d) and have a reactive group comprising an alcoholic hydroxyl group, a primary or secondary amino group or an isocyanate group.

2. Sterile nonwovens obtained by the processes of claim 1.

3. Medical or hygiene articles produced from the sterile nonwovens of claim 2.

4. Aseptically packaged articles as claimed in claim 3.

5. A process for producing sterile nonwovens, according to claim 1, which additionally comprises surrounding the nonwoven articles with packaging impervious to the penetration of microorganisms prior to irradiation.

* * * * *